(12) United States Patent
Rodriguez

(10) Patent No.: US 7,858,602 B2
(45) Date of Patent: Dec. 28, 2010

(54) THERAPEUTIC AND PROPHYLACTIC USES OF CELL SPECIFIC CARBONIC ANHYDRASE ENZYMES IN TREATING AGING DISORDERS DUE TO OXIDATIVE STRESS AND AS GROWTH FACTORS OF STEM CELLS

(76) Inventor: Victorio C. Rodriguez, 7791 Hoertz Rd., Parma, OH (US) 44134

( * ) Notice: Subject to any disclaimer, the term of this patent is extended or adjusted under 35 U.S.C. 154(b) by 363 days.

(21) Appl. No.: 11/801,870

(22) Filed: May 12, 2007

(65) Prior Publication Data

US 2007/0224182 A1 Sep. 27, 2007

Related U.S. Application Data

(63) Continuation-in-part of application No. 10/858,091, filed on Jun. 1, 2004, now Pat. No. 7,256,184, which is a continuation-in-part of application No. 10/077,719, filed on Feb. 15, 2002, now Pat. No. 6,821,997, which is a continuation-in-part of application No. 09/688,290, filed on Oct. 16, 2000, now abandoned.

(51) Int. Cl.
| | | |
|---|---|---|
| A61K 31/593 | (2006.01) |
| A61K 33/30 | (2006.01) |
| A61K 31/315 | (2006.01) |
| A61K 31/405 | (2006.01) |
| A61K 31/23 | (2006.01) |
| A61K 31/145 | (2006.01) |
| A61P 25/28 | (2006.01) |

(52) U.S. Cl. ............ 514/167; 514/168; 514/420; 514/494; 514/548; 514/665; 514/879; 424/641; 424/643

(58) Field of Classification Search ......... 514/167–168, 514/171, 400, 419, 546–548, 567, 729, 879, 514/420, 494, 665; 424/641, 643
See application file for complete search history.

(56) References Cited

U.S. PATENT DOCUMENTS

| | | | |
|---|---|---|---|
| 4,791,099 A | 12/1988 | Aroonsakul |
| 4,837,219 A | 6/1989 | Hutterer |
| 4,897,389 A | 1/1990 | Aroonsakul |
| 5,470,846 A | 11/1995 | Sandyk |
| 5,939,407 A | 8/1999 | Landfield |
| 5,972,684 A | 10/1999 | Bandman et al. |
| 6,013,623 A | 1/2000 | Spector et al. |
| 6,025,395 A | 2/2000 | Breitner et al. |
| 6,048,553 A | 4/2000 | Beckett |
| 6,150,346 A | 11/2000 | Knutson et al. |
| 6,262,041 B1 | 7/2001 | Serbinova |
| 6,821,979 B2 * | 11/2004 | Alkon et al. ........... 514/263.31 |
| 6,821,997 B1 | 11/2004 | Rodriguez |
| 6,927,231 B2 | 8/2005 | Droge |
| 6,930,099 B2 | 8/2005 | Petrus |
| 7,166,569 B2 | 1/2007 | Fahy |
| 7,232,809 B2 | 6/2007 | Murphy et al. |
| 7,256,184 B2 | 8/2007 | Rodriguez |
| 2004/0235889 A1* | 11/2004 | Sun et al. ................ 514/310 |

OTHER PUBLICATIONS

Gauthier et al., "Can we do better in developing new drugs for Alzheimer's disease?" Alzheimer's & Dementia, vol. 5, pp. 489-491 (2009).*
Shah, R.S. et al., "Current approaches in the treatment of Alzheimer's disease," Biomedicine & Pharmacotherapy, vol. 62, pp. 199-207 (2008).*
Shah, R.M. et al., "Strategies to maximize the encapsulation efficiency of phenylalanine ammonia lyase in microcapsules," International Journal of Pharmaceutics, vol. 356, pp. 61-68 (2008).*
Abstract—"Age-dependent enzymatic changes in human cerebral cortex" by Reichlmeier, K., Aktuelle Gerontol, Aug. 1978, 8(8):441-8.
Abstract—"Neurochemical findings in the aging brain" by Meier-Ruge, et al., Adv, Biochem Psychcopharmacol, (1980).
Abstract—"Carbonic anydrase III. Oxidative modification in vivo and loss of phosphatase activity during Aging " by Cabiscol, et al., J. Biol. Chem. Jun. 16, 1995;270(24):14742-7.
Abstract—"Intracellular zinc depletion induces caspase activation and p21 Waf1/Dip1 cleavage in human epithelial cell lines" by Chai, et al, J Ifect Dis Sep. 2000:182 Suppl 1:S85-92.
Abstract—"Efficacy of exogenous oral zinc in treatment of patients with carbonic anhydrase VI deficiency"by Henkin, et al., Am J Med Sci Dec. 1999;318(6):392-405.

(Continued)

Primary Examiner—John Pak

(57) ABSTRACT

A method for the treatment and prophylaxis of conditions of aging due oxidative stress and as growth factors of stem cells. Such conditions due to oxidative stress are associated with a decreased presence of one or more cell-specific carbonic anhydrase enzymes in the tissue of a subject. Such conditions include but are not limited to alzheimer's disease, parkinson's disease, multiple sclerosis, autism, lou gehrig's disease, huntington's disease, diabetes mellitus, amyloid diseases, atherosclerosis, arthritis, osteoporosis, cystic fibrosis. The method comprises administering to the patient a pharmaceutically effective, non-toxic amount of one or more compounds that increases the presence of one or more Carbonic Anhydrase Isozymes whose levels have been reduced in the subject. Such compound maybe the Cell Specific Carbonic Anhydrase Enzymes, a compound that when absorbed reacts or dissociates to form cell specific carbonic enzymes or a compound that when administered promotes the natural generation of the cell specific carbonic anhydrase enzymes within the subject.

Figure 3:
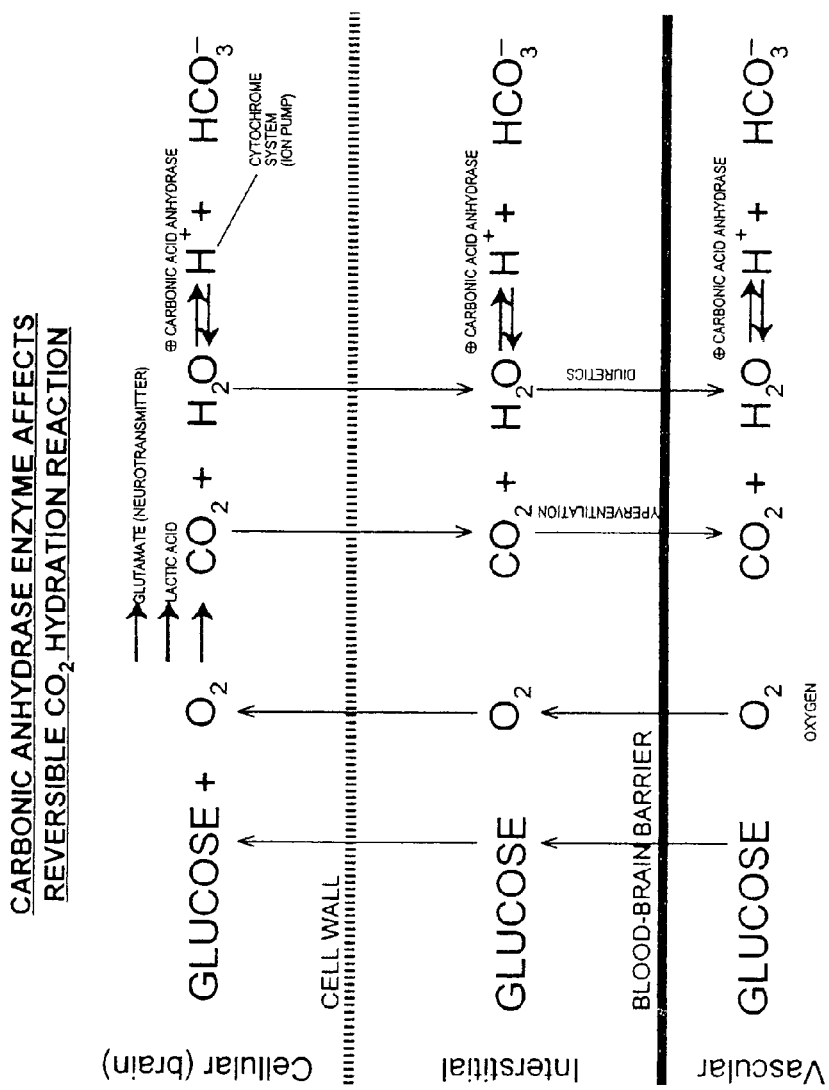

This method also uses one or more cells specific carbonic anhydrase as growth factors of stem cells for replacing tissues due to injuries or diseases in humans.

These methods includes the administering of these compounds over an extended period of time ranging from 6 months until the subject dies.

8 Claims, 3 Drawing Sheets

OTHER PUBLICATIONS

Abstract—"Current status of metals as therapeutic targets in Alzheimer's disease" by Finefrock, et al., *Journal of the American Geriatrics Society*, (Aug. 2003) 51 (8) 1143-8.

Abstract—"Addition of carbonic anhydrase augments extracellular pH buffering in rat cerebral cortex" by Huang, et al., *J. Neurophysiol*, Oct. 1995;74(4):1806-9.

Abstract—"Nonsteroidal anti-inflammatory drugs activate carbonic anhydrase by a direct mechanism of action" by Puscas, et al., *Pharmacol. Exp Ther*, Jun. 1996;277(3):1464-6.

Abstract—"Effects of rofecoxib or naproxen vs. placebo on Alzheimer disease progression" by Aisen, et al., *JAMA The Journal of the Amercian Medical Association* (2003), 289(21), 2819-2826.

Abstract—"Defective phorbol ester-stimulated secretion of .beta.-amyloid precursor protein from Alzheimer's disease fibroblasts" by Bergamaschi, et al., *Neuroscient Letters*, (1995), 201(1), 1-4.

Alzheimer's Medication Fact Sheet—National Institute of Aging Retrieved from the Internet on Apr. 6, 2010.

Alzheimer's Disease—drugs slows progression of disease—Mayo Clinc Retrieved from the Internet on Apr. 4, 2010.

Smell identification test—Alzheimer's disease-Velayudhan L et a J Clin Physcopharmacol. Aug. 2009;29(4):387-90.

Acetylcholine—Wikepedia Retrieved from the Internet on Mar. 20, 2010.

Histamine—Wikedpedia Retrieved from the Internet on Mar. 24, 2010.

Phenylketonuria—Medline Plus Retrieved from the Internet on Apr. 27, 2010.

Acetylcholine synthesis and neuron differentiation- Biagoni et al-Int J Dev Biol 2000;44(6):689-97.

Testosterone no Estrogen Lackey—Protects Brain in its own right Alzheimer's Research Forum Retrieved from the Internet on Jun. 5, 2010.

* cited by examiner

CARBONIC ANHYDRASE ENZYMES

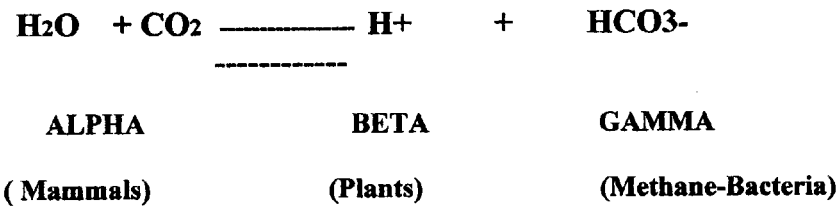

| ALPHA | BETA | GAMMA |
|-------|------|-------|
| (Mammals) | (Plants) | (Methane-Bacteria) |

ALPHA CARBONIC ANHYDRASE ENZYMES
Cell Specific Carbonic Anhydrase produces H+ (Hydrogen Ions) acted upon by the Cytochrome System and utilized as:

A. In the Mitochondria (Cytochrome System)
   Glucose + $O_2$ ——— $H_2O$ + $CO_2$
   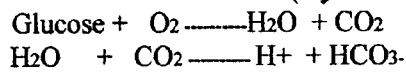

Hydrogen ion produced is utilized as fuel of the ion pump that maintains the integrity of the cell wall membrane B. In the Mitochondria (Cytochrome System)
   H+ ( Hydrogen Ion) plus ADP(adenosine Diphosphate)------ATP
   (adenosine triphosphate) Hydrogen ion produced is utilized as fuel for other Cellular functions C. In the Mitochondria (Cytochrome System)
   Glucose + O2———H2O + CO2 + (O2)-2 (Reactive Oxygen) 1 to 5%
   O2(Oxygen) minus 2 electrons ------- (O2)-2 (Reactive Oxygen)

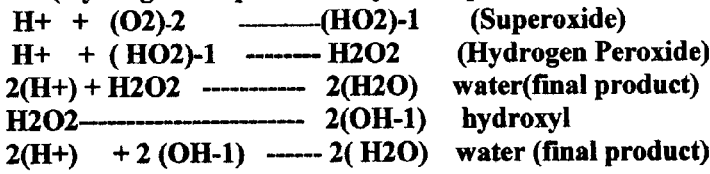

Deficiencies of Hydrogen ions produced due to decreased levels of Cell Specific Carbonic Anhydrase Enzymes leads to diseases or conditions associated with Oxidative Stress due to oxidative damages on all cellular and non-cellular Structures,and conditions due to cellular death as a result of hydrogen fuel deficiency

FIG. 1

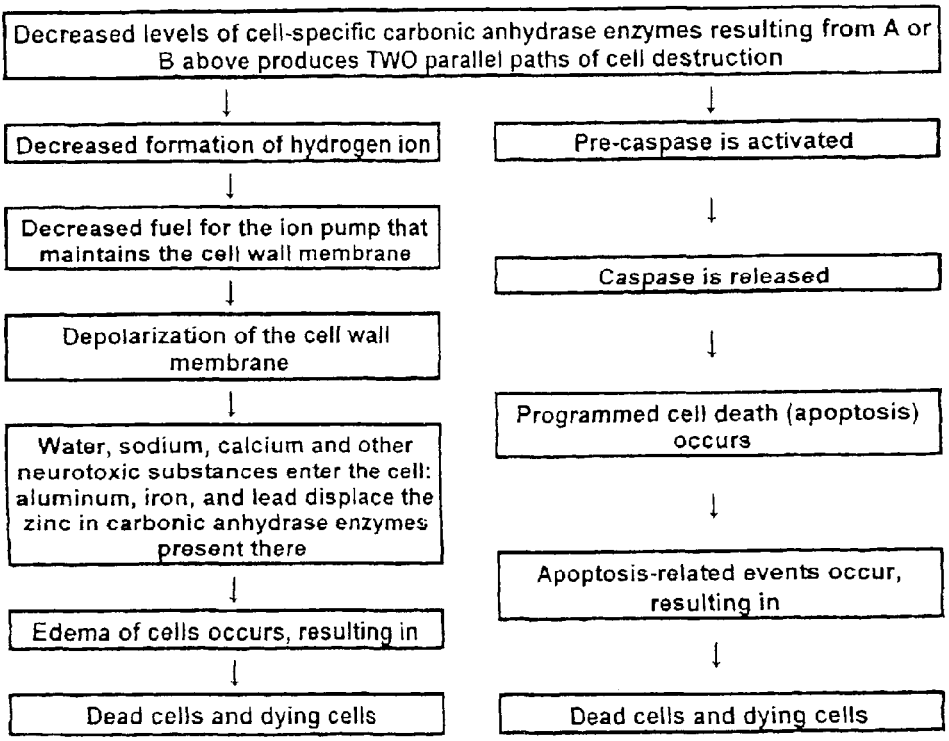
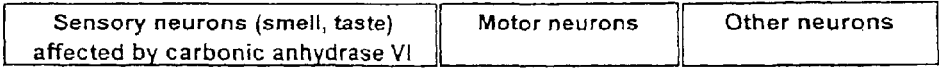
Fig. 2

THERAPEUTIC AND PROPHYLACTIC USES OF CELL SPECIFIC CARBONIC ANHYDRASE ENZYMES IN TREATING AGING DISORDERS DUE TO OXIDATIVE STRESS AND AS GROWTH FACTORS OF STEM CELLS

CROSS REFERENCE TO RELATED APPLICATIONS

THIS APPLICATION IS A CONTINUATION IN PART OF U.S. patent application Ser. No. 10/858,091 FILED ON JUN. 1, 2004, now U.S. Pat. No. 7,256,184, WHICH IS A CONTINUATION IN PART OF U.S. application Ser. No. 10/077,719 FILED ON FEB. 15, 2002 now U.S. Pat. No. 6,821,997 WHICH IS A CONTINUATION IN PART OF U.S. application Ser. No. 09/688,290 FILED ON OCT. 16, 2000 NOW ABANDONED.

FIELD OF THE INVENTION

This invention deals with the therapeutic and prophylactic uses of Cell Specific Carbonic Anhydrase Enzymes in the treatment of aging disorders due to oxidative stress-related disorders, oxidative-related neurological disorders and as growth factors of stem cells.

BACKGROUND OF THE INVENTION

Carbonic Anhydrase Enzymes are ancient Zinc enzymes which are further divided into Alpha, Beta and Gamma carbonic anhydrase enzymes. The Alpha group belongs to mammals and are thought to be 200 TO 300 million years old. The Beta group belongs to plants. They are thought to be about 3.5 billion years old. The Gamma group belongs to the methane-producing bacteria which are also thought to be about 4 billion years old. These Carbonic Anhydrase Enzymes are structurally distinct from each other except they contain the same Zinc ion and catalyzing the same reversible reaction $H_2O + CO_2 \rightleftharpoons H^+ + HCO_3^-$ Carbonic anhydrase enzymes are the fastest enzymes doing 10(6) power reactions per second. In mammals their activities are not limited to the acid base balance, maintaining the $PO_2/CO_2$ ratio, ester hydrolysis, ion transport, phosphatase activity, $CO_2$ hydration, maintaining the equilibrium between $H_2O$, $CO_2$ and $H^+HCO_3^-$ in all spaces, cellular, interstitial and vascular spaces as illustrated in FIG. 3.

In mammals Carbonic anhydrase isozymes are further divided into: Carbonic Anhydrase I to XXV:

CA I—are cystosolic enzymes are mostly found in Red blood Cells, vascular endothelial cells, gastrointestinal mucosa
CA II—cystosolic enzyme found in almost all tissues but mainly in the Brain, Bones, Kidneys
CA III—cystosolic enzyme mostly found in muscles, synovial tissues
CA IV—is membrane bound, found in the capillary endothelial cells, brain, kidney
CA V—mitochondrial—beta cells, pancreas
CA VI—secretory mostly found in tears saliva, milk, mammary gland, nasal and repiratory mucosa
CA VII—cystosolic Enzyme—(brain) hippocampal, CA I pyramidal cells, salivary
CA VIII—CARP (carbonic anhydrase related protein)
CA IX—Membrane Bound MN/protein (tumor associated)-Catalytic
CA X—CARP (carbonic anhydrase related protein)
CA XI—CARP (carbonic anhydrase related protein)
CA XII—Membrane Bound
CA XIII—cystosolic
CA XIV—membrane bound Normal aging in humans is recognized as producing some or all of the following typical physiological results but not limited to:
1. Brain weight is reduced by 15%
2. Blood flow to the brain is reduced by 20%
3. Body water content is reduced by 18%
4. Body weight is reduced by 12%
5. Nerve conduction velocity is reduced by 10%
6. Number of nerve fibers is reduced by 37%
7. Decreased amounts of enzymes and coenzymes
8. Decreased amounts of neurotransmitters
9. Depletion of phosphorelative enzymes
10. Apostosis-chronic neuronal atrophy Signs and Symptoms of Human aging includes but are not limited to:
1. Increased body fat
2. Decreased energy
3. Decreased sexual performance
4. Decreased libido
5. Decreased skin elasticity
6. Decline in mental function
7. Decline in vision/eyesight
8. Joint pain
9. Decreased lean muscle
10. Decreased bone mass
11. Decline in memory
12. Diminished immune system
13. Wrinkles and cellulite
14. Decreased cardiac output
15. High blood pressure
16. undesirable cholesterol
17. Decreased exercise performance
18. Slower rate in healing
19. Decline in taste/smell
20. Frailty and others In describing their work in an article entitled "Studies on age-Dependent Ozonide Changes in Human Cerebral Cortex," (by Reichlmeier K., Ermini M., and Schlecth H. P.—Aktuellel Gerontl 1978 Aug. 8(8):44-8) the authors report that they investigated the activity of various enzymes of human brains obtained at autopsy and covering an age range of 19 to 91 years. Protein Kinase, which mediates the information carried by the second messenger, cyclic AMP (3',5'-cyclic adenosine monophosphate), does not show age-related changes of basal activity. Cyclic AMP-dependent activation of protein kinase remains constant up to 60 years of life but it undergoes a distinct and progressive decline between 60 and 90 years. In the corpus striatum, no age related changes of cyclic AMP-dependent protein activity were observed. The activity of carbonic anhydrase exhibits, in both human cortex and corpus striatum, an age-dependent decrease that also begins after the sixth decade.

Aging is further divided into primary aging and secondary aging (accelerated). Primary Aging is caused mainly in the inherent progressive decrease activities of the genes that regulates the cell. While secondary aging (accelerated aging) is caused mainly by oxidative stress. Oxidative stress is mainly caused by external factors such as environmental factors, toxic materials, ionizing radiations, or any condition or disease that alters the vascular endothelium and the cell wall membrane. These altered conditions allows the entry of substances that will displace the zinc from cell specific carbonic anhydrase enzymes leading to the decreased level of cell specific carbonic anhydrase enzymes hence leading to cellular death.

In Aging there is an age-associated dysregulated inflammatory and immune response leading to an increase production of PGE2 and Cyclooxygenase. They inhibit the production of Cell Specific Carbonic Anhydrase Enzymes IN Brain Behav Immun. 2004 November; 18(6):487-94 by Wu D, Meydani S N Mechanism of age-associated up-regulation in macrophage PGE2 synthesis Many physiological functions of the body change during the aging process. Dysregulated immune and inflammatory responses have been well documented in both humans and animals. The investigation into the cellular and molecular mechanism underlying these disorders has provided compelling evidence that up-regulated cyclooxygenase (COX2) and its product particularly prostaglandin (PGE2) lay a critical role in the age-associated dysregulation of the immune and inflammatory responses. Studies have shown that increase production of PGE2 by old macrophages contributes to the suppression of T cell function. Decreasing production of PGE2 have shown enhanced T mediated cell function. Upon stimulation old mice macrophages generate more ceramide which in turn augments stimulated COX2 expressions and PGE2 production.

Crit Rev Immunol. 2004; 24(5):349-62 by Trottein F, Faveeuw C, Gosset P, Angeli V Role of the D prostanoid receptor 1 in modulation of immune and inflammatory responses.

Prostaglandins (PGS) are potent eicosanoid lipid mediators derived from phospholipase released arachidonic acid, which are involved in numerous homeostatic biological functions and inflammation. Along with their role in inflammatory responses evidence strongly suggest that PGS, including PGD2 are part of the complex regulatory network that modulates the immune system. PGE2 is the major prostaglandin activated by mast cells in allergic diseases.

In Arthritis Res. 1999; 1(1):63-70. Epub 1999 Oct. 14. by Tetlow L C, Wooley D E The effects of alpha, 25-dihydrovitamin D3 on matrix metalloproteinase and prostaglandin E (2) production by cells of rheumatoid lesion. Vitamin D3 modulate the effect of Matrix metalloproteinase. Matrix metalloproteinase and PGE2 are chondrolyic enzymes which plays a major role in the breakdown in the rheumatoid joint.

Arthritis Rheum. 1999 December; 42(12):2561-8 by Yaron I, Shirazi I, Judovich R, Levartovsky D, Caspi D, Yaron D Fluoxetine and aminitriptylline inhibit nitric oxide, Prostaglandin PGE2 and hyaluronic acid production in human synovial cells and synovial tissue cultures. Their conclusion; Inhibition of NO and PGE2 production by connective tissue cells is a mechanism by which some antidepressant medications may affect pain, articular inflammation.

In Cystic Fibrosis

Eur J Cell Biol. 2002 August; August; 81(8):437-47

Targeting of Carbonic Anhydrase IV to plasma membranes is altered in cultured human pancreatic duct cells expressing a mutated (deltaF508) CFTR—by Fanjul M, Salvador C, Alvarez L, Cantet S, Hollande E Their studies showed that the level Carbonic Anhydrase IV is decreased resulting in the decreased secretion of Cl- and HCO3-ions as well as defective targeting of other proteins. This is due to a 6-10 fold fewer cells in the CFPAC-1 cell lines.

Antibodies to Cell Specific Carbonic Anhydrase Enymes are produced as a result of an immunologic response to defend themselves. This is in response to the progressive cell death as a result of the progressive decrease in the level of cell specific carbonic anhydrase enzymes in a subject due to oxidative stress and aging or conditions or diseases that decreases the level of cell specific carbonic anhydrase enzymes in the tissue of a subject as illustrated in FIG. 2

Antibodies to Carbonic anhydrase has been found in systemic lupus erythematosus and other rheumatic diseases; Arthritis Rheum. 1992 autoantibodies of CA I, CA II isoform, in Systemic Lupus rythematosus, scleroderma, and polymyositis in their sera. January; 35(1):73-82 by Itoh Y, Reichlin M.

In Dermatol Sci. 1991 May; 2(3): 147-54 by Inagaki Y, Jinno-Yoshida Y, Hamasaki Y, Ueki H. they also found auto Antibodies to CA I, CA II isoform in patients sera in Syogren's Disease, Renal tubular acidosis and systemic Lupus Erythematosus.

Autoimmunity. 2003 March; 36(2):85-9 by Alessandri C, Bombardieri M, Scrivo R, Viganego F Conti F, deLuca N, Riccieri V, Valeseni G deals with the presence of anti-Carbonic anhydrase antibody as possible pathogenic role of anti-CA II in the development of lung damage in systemic sclerosis (SSC) disease.

In Clinical Chemistry. 2003; 49:1221-1223—Effect of Anti-Carbonic anhydrase antibodies on Carbonic anhydrase I and II by Francesco Botre, Claudio Botre, Elissabetta Podesta, Mauro Podda and Pietro Invernizzi. they isolated CA I, II isoform antibodies in patients with systemic lupus erythematosus, polymyositis, systemic sclerosis, endometriosis syogrens, disease, idiopathic chronic pancreatitis, primary biliary cirrhosis, and autoimmune cholangitis.

Int J Mol Med. 2002 May; 9(5):499-502 by Andoh A, Fujiyama Y, Yoshioka U, Sasaki M, Araki Y Tsugikawa T—discusses the presence of Anti-carbonic anhydrase II antibodies in patient with ulcerative colitis.

Growth Factors are useful in the enhancement maintenance proliferation and differentiation of stem cells to specific cells or tissues.

IN Proc Soc Exp Biol Med. 1987 January; 184(1):24-30 by Cavral A T R, Hewett-Emmett D Welty R J, Castor C W Effects of human Carbonic anhydrase III on synovial and muscle fibroblastic glycosaminoglycanl metabolism They investigated the ability of CA III, isolated from adult human skeletal muscle to regulate cell growth and glycosaminoglycan formation in connective tissue cells. Cell culture experiments showed that exposure to CA III by synovial connective tissue fibroblast, they were increased by 2 to 12 fold, also increased hyaluronic acid synthesis. Also exposure to CA III leads to an increase in muscle fibroblast by 20-45%, synovial fibroblasts by 16-70%.

Endocrinology. 1997 November; 138(11):4852-7. by Biskobing D M, Fan D, Fan X, Rubin J. Induction of carbonic anhydrase II expression in osteoclast progenitors requires physical contact with stromal cells. It tells that osteoclast progenitors requires the physical communication of Carbonic anhydrase II with stromal cells for them to differentiate to osteoclast.

j. Histochem Cytochem. 2004 August; 52(8):1057-62 by Kimoto M, Iwai S, Maeda T, Yura Y, Fernley R T, Ogawa Y Tells us that CA VI plays A role in olfactory function as a growth factor in the maturation of the olfactory epithelial cells.

Am J Med Sci. 1999 December; 318(6):39-405—by Henkin R I, Martin E M, Agarwal R P Efficacy of exogenous oral Zinc in treatment of patients with Carbonic Anhydrase VI deficiency.

Tells us about the use of oral Zinc in stimulating the production of CA VI which promotes the growth of taste buds.

In Transplantation. 2001 Jun. 27; 71(12):1735-40 by Nakano K, Migita M, Mochisuki H Shimada T Bone Marrow Transplantation was reported effective in preventing the progression of neurological deterioration of lysosomal disease. They concluded that the bone marrow contains cells capable of differentiating into oligodendrocytes and astrocytes.

and microglia when exposed to brain microenvironment.

J Histochem Cytochem. 2004 August; 52(8:1107-12 by Leinonem J S, Saari K A, Seppanem J m, Myllyla H M, Rajaniemi their studies shows that CA VI maybe a growth factor in the respiratory epithelium Brain Res Dev Brain Res. 1992 Jun. 19; 67(2):257-63 by Cammer W, Zhang H shows that Carbonic anhydrase are distinct precursors of astrocytes and oligodendrocytes in the forebrains of neonatal and young rats.

The American Society for Biochemistry and Molecular Biology, Inc. Volume 271, Number 17, Issue of Apr. 26, 1996 pp. 10169-10174 Peter H. Frederikse, Donita Garland, J. Samuel Zigler Jr., Joram Piatigorsky In their studies, oxidative stress increases production of B-Amyloid Precursor Proteins and B amyloid (Ab) in mammalian lenses. Amyloid diseases are characterized by protein aggregations linked to oxidative stress.

Rinsho Byori. 2003 February; 51(2):140-5

Amyloidosis and Oxidative Stress-Nakamura M, Ando Y.

Their studies on oxidative stress have revealed that free radical injury Appears to be involved in either the amyloid formation process or in Post-fibrillar modification in several types of amyloidosis, the role of Oxidative stress in the pathogenesis of dialysis-related amyloidosis And familial amyloidotic polyneuropathy Journal of Neuroinflammation 2004, 1:21 doi:10.1186/1742-2094-1-21 Yuemang Yao, Cinzia Chinnici, Hanguan Tang, John Q Trajanowski, Virginia My Lee, Domenico Pratico Brain Inflammation and oxidative stress in a transgenic mouse model of Alzheimer-like Brain Amyloidosis Their studies implicates an increasing body of evidence which implicates Both brain inflammation and oxidative stress in the pathogenesis of alzheimer's disease.

In Autism there are evidences that Mercury (HG), a neurotoxic metal causes Autism, Mercury displaces the Zinc ion found in the Carbonic Anhydrase Isozymes resulting in their decreased level.

In U.S. Pat. No. 6,297,212 and U.S. application Ser. No. 09/933,309-Gregory Fahy he used Growth hormone and dehydroepiandrosterone (DHEA) in regenerating the involuted thymus in restoring the immune system Below are selected Patent References, other patent references published on diseases of oxidative stress are incorporated in this invention 1. U.S. Pat. No. 6,306,844—use of 2 alpha methyl-19-nor 20(s)1,25-dihydroxyvitamin D3 to increase bone strength
2. U.S. Pat. No. 6,150,346—Method & Composition for treating or preventing osteoporosis
3. U.S. Pat. No. 6,673,782—use of 1,25-dihydroxyvitamin D3-treatment of systemic lupus erythematosus
4. U.S. Pat. No. 7,078,059—treatment of bone disease
5. U.S. Pat. No. 6,828,331—growth hormone secretagogues
6. U.S. Pat. No. 5,895,652—metabolic adjuvanation and cellular repair
7. U.S. Pat. No. 6,297,212—Growth hormone therapy and related methods & Related methods pharmaceutical compositions
8. U.S. Pat. No. 5,763,429—Method for treating prostatic diseases using Vitamin D analogues
9. U.S. Pat. No. 5,763,428—method of treating skin disorders with Vitamin D4
10. U.S. Pat. No. 6,147,064 method for treating psoriasis
11. U.S. Pat. No. 5,700,790—Prevention and treatment of myocardial failure
12. U.S. Pat. No. 6,930,099—composition for the treatment and prevention of endothelial dysfunction

SUMMARY OF THE INVENTION

The present invention provides methods for the treatment and prophylaxis of diseases or conditions of aging disorders due to oxidative stress and as growth factors of stem cells. These conditions are associated with the decreased level Of one or more cell specific carbonic anhydrase enzyme in the tissue of a subject. This decreased of carbonic anhydrase isozymes in the tissue of a subject leads to oxidative damages on all cellular and non cellular structures. This also leads to the decreased fuel of the ion pump that maintains the cell wall membrane of cellular elements leading to their death. These leads to diseases or conditions that include but not limited to atherosclerosis, osteoporosis, systemic lupus erythematosus amyloidosis, arteriosclerosis, rheumatoid arthritis, osteoarthritis, cardiomyopathies, endothelial dysfunctions, myocyte dysfunctions cystic fibrosis, thrombosis, integumentary dysfunctions, lipid dysfunctions ischemic heart disease, congestive heart failure, diabetes, hypertension. This invention also include chronic neurodegenerative disorders including but not limited to dementia, Alzheimer disease; multiple sclerosis, Lou Gehrig disease, parkinson's disease, autism. This invention includes all other diseases or conditions associated with oxidative stress. These comprises assaying for the decreased levels of one or more cell specific carbonic anhydrase enzymes in the tissue of a subject and then administering one or more compounds that increases the level of one or more cell specific carbonic anhydrase enzymes that are present at reduced levels in the tissue of the subject. In certain embodiments the tissue is blood, cerebro-spinal fluid, or the biopsied tissue of the subject. A finding that the tissue level of one or more carbonic anhydrase enzymes is decreased is based upon the comparison with a control value derived from a healthy young subjects. In certain embodiments the method comprises administering one or more Carbonic Anhydrase Isozymes either synthetically produced or naturally produced to the subject. In another embodiment comprises administering one or more compounds that induce or promotes the generation of one or more carbonic anhydrase enzymes that are present at reduced levels in the subject. In another embodiment the method comprises administering one or more compounds that when absorbed by a tissue of a subject reacts or dissociates to form one or more carbonic anhydrase isozymes that are present at reduced levels in the subject. In another embodiment the method comprises administering Carbonic anhydrase isozymes I, II, III, IV, V, VI, VII as growth factors for stem cells. In another embodiment administering one or more compounds that induce or promotes the natural generation of one or more Cell specific Carbonic Anhydrase I, II, III, IV, V, VI and VII as growth factors of Stem cells in treating damaged or diseased cells or tissues. In certain embodiments, these, one or more compounds are administered over an extended period of time ranging from 6 months until the subject dies.

BRIEF DESCRIPTIONS OF THE DRAWINGS

FIG. 1. Illustrates Carbonic Anhydrase Enzymes

FIG. 2. illustrates the physiology of Carbonic anhydrase Isozymes

FIG. 3. illustrates the pathophysiology of Human diseases and disorders of Carbonic anhydrase isozymes

DETAILED DESCRIPTION OF THE INVENTION

The present invention will now be described by reference to more detailed embodiments, with occasional reference to the accompanying drawling. The invention may, however, be embodied in different forms and should not construed as limited to the embodiments set forth herein. Rather, these embodiments are provided so that the disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise. All publications patent applications, patents, and other references mentioned herein are incorporated by reference in their entirety.

The following represents an essential chemical reaction that takes place in human tissue. Glucose (Within the Cells)+ Oxygen—$H_2O+CO_2$—H++$HCO_3$—Carbonic Anhydrase present (reversible reaction)

Eq. (1)

Glucose is irreversibly oxidized within the cells to produce water and carbon dioxide. In the presence of a catalyst, especially a carbonic anhydrase enzyme (of which several forms exist, of which the form present depends upon the type of tissue cell present), the water and carbon dioxide reversibly produce a hydrogen ion and a bicarbonate ion.

Carbonic anhydrase is a Zinc-containing enzyme that catalyses the reversible $CO_2$ hydration reaction illustrated in Eq. 1. The mitochondria of cells of different tissues and organs produce different specific carbonic anhydrase enzymes that maintain the equilibrium of the above equation in all spaces-cellular, interstitial, and vascular—as illustrated in FIG. 3. At least seven carbonic anhydrase variants called "S" have been identified. The literature may refer to these as "carbonic anhydrase I through VII" or "CAS-I-VII". WE refer to this selectivity as "cell specific" and the particular carbonic anhydrase present as being a "Cell specific carbonic anhydrase enzyme".

Hydrogen ion produced by carbonic anhydrase enzymes is acted upon by the cytochrome system, which is then utilized as the energy source of the ion pump that maintains the integrity of the cell membrane comprising and enclosing each cell. It is also thought to be the source of the brain's electric current. The process is schematically illustrated in FIG. 1, presented here with no further discussion.

Disruption of the process that include Eq. 1 causes depolarization of the cell wall membrane, hence (Na), water (H.sub.2O), and other chemicals can enter the cell in uncontrollable amounts and potassium (K) can exit uncontrollably, leading to the death and destruction of the involved cells; cellular edema follows. As the edema progresses, the cell dies. Along with the progressive and gradual death of cells, gliosis follows—hence aging in the brain occurs (FIG. 2).

In this newly presented INSTANT INVENTION as illustrated in FIG. 1B. Aside from being the fuel of the ion pump, hydrogen ions produced by cell specific carbonic anhydrase enzymes are acted upon by the cytochrome system and are utilized as fuel (H++ADP (adenosine diphosphate—ATP (adenosine triphosphate) for all other cellular functions.

In this newly presented INSTANT INVENTION as illustrated in FIG. 1C, In aerobic respiration, Oxygen is needed in utilizing glucose as the source of energy. As a by product, Oxygen free radicals are produced.

In the Mitochondria 1% to 5% of Oxygen free radicals are formed. Glucose+$O_2$—$H_2O+CO_2+(O_2)-2$ (reactive Oxygen Oxygen minus (2) electrons—$(O_2)-2$ In the Cytochrome System found inside the Mitochondria, Hydrogen ions produced by Carbonic Anhydrase Isozymes combines with reactive oxygen.

This is illustrated in the following steps:

1. $H_2O+CO_2$—H++$(HCO_3)-1$—reversible reaction Carbonic anhydrase isozymes)

Hydrogen ions produced: (from Carbonic Anhydrase isozymes)

2. H++$(O_2)-2$—$(HO_2)-1$ (superoxide)
3. H++$(HO_2)-1$—$H_2O_2$ (Hydrogen peroxide)
4. $H_2O_2$—2(OH−1) (Hydroxyl)
5. 2(H+)+2(OH−1)—2($H_2O$) (water)-final product Hydrogen ions produced by carbonic anhydrase enzymes neutralizes all Reactive Substances.

Lack of Hydrogen ions due to deficiencies of Cell specific Carbonic anhydrase enzymes as a result of normal aging and as a result of conditions due accelerated aging (FIG. 2) do not complete the above reactions, the final product being water ($H_2O$). This leads to the increase levels of reactive oxygen.

These reactive oxygen causes lipid oxidation, protein oxidation, DNA fragmentations, disruption of the cell wall membrane and binds with almost all molecules in the body. These reactive oxygen species and other reactive substances are implicated with diseases or conditions associated with oxidative stress, aging and cancer.

Hydrogen ions acted upon by the cytochrome system produced by Cell Specific Carbonic anhydrase Enzymes are also utilized by proteins to make them more stable. It has been shown that removal of the Hydrogen Bonds leads to protein Misfolding leading Diseases and abnormal conditions in a subject which includes amyloidosis J Theor Biol. 2002 Apr. 21; 215(4):399-404

Hydrogen Bonds and the catalytic mechanism of human carbonic anhydrase II—by Thomas S Tells us about the production of Hydrogen Bonds by Carbonic anhydrase II making a substance more stable Oxidative stress is associated with an increase in the level Of amyloid precursor proteins leading to amyloid depositions all over the body of a subject.

Prior Art

Carbonic anhydrase enzyme has been used to augment the extracellular ph buffering in the cerebral cortex of rats (Journal of Neurophysiology 1995 Oct. 74(4):1806-9. It is known that the blood brain barrier in animals is incomplete compared to that of humans where the blood brain barrier is complete and a formidable barrier to chemical transport. Substances that prove efficacious in affecting the brain chemistry of animals are not necessarily efficacious in the brains of human beings because they cannot pass through the more complete blood brain barrier in humans. Although some researchers equivocate on this concept most of the medical community accepts the idea that carbonic anhydrase enzymes traverse the blood brain barrier in humans as fact, especially regarding the carbonic anhydrase enzyme referred to as CA-II As far as can be determined in the literature, cell specific carbonic anhydrase enzymes have never been used to restore to a higher level the carbonic anhydrase enzymes that are lacking due to decreased levels due to normal aging and diseases associated with oxidative stress. At least some of the carbonic anhydrases have been extracted from animal tissue, isolated, and studied for molecular structure. This shows that the enzymes can be isolated and made available for administration to a patient for therapeutic or prophylactic treatment.

In U.S. Pat. No. 5,972,684, Badman et al. tell us:

Eight enzymatic and evolutionary related forms of carbonic anydrase enzymes are currently known to exist in humans; three cystosolics (CA I, CA II, CA III), two membrane bound forms (CA IV, and CA VII), a mitochondrial form (CA V), a secreted salivary form (CA VI) and a yet uncharacterized Isoforms show a characteristic motif. (See, e.g., http://expassy.hcuge.ch). Though the isoenzymes CA I, CA II, and bovine CA III have a similar secondary structure and polypeptide chain fold, CA I has 6 tryptophans, CA II has 7 and CA III has 8 (Boren, K et al. (1996) Protein Sc. 5(12): 2479-2484). CA II is the predominant CA isoenzyme in the brain of mammals.

Inhibition and activation of CA provide information about CA structure and activity. Vasodilating prostaglandins E1, E2, E12 inhibit CA in vitro and in vivo and may inhibit the involvement of CA in gastric acid secretion. Nonsteroidal anti-inflammatory drugs which reduce the activity of cyclooxygenase and prostaglandin production have also been observed to activate CA I, and CA II in dose dependent non competitive manner. The pre-prostaglandin cyclooxygenase appears to maintain an inverse relationship with CA, probably mediated by the ph variations associated with carbonic anhydrase activity.

(Puscas, I (1996) J. Pharmacol. Exp. Ther. 277(3):1464-1466). Both prostaglandins E2 and E12 inhibit gastric acid output. Prostaglandin E2 inhibits egress of norepinephrine from sympathetic nerve terminals.

The Bandman et al. teaches another carbonic anhydrase enzyme, CA-VIII, the subject of their patent. The present patent does not deal with nor address CA-VIII Patients having a carbonic anhydrase VI (CA-VI) deficiency have been treated with orally administered Zinc in an effort to stimulate the synthesis/secretion of CA-VI and the successful results were reported in the American Journal of Medical Science (Efficacy of Exogenous oral Zinc in the treatment of patients with carbonic anhydrase deficiency, by Henkin R. I., Martin, B. M., l and Agarwal, R. P.—Am J Med Sci 1999 Dec. 3; 18(6):392-405). The Carbonic Anhydrase VI produced acted as growth factors of stem cell taste buds in Patients. Thus it is shown that the synthesis/secretion of carbonic anhydrase can, indeed, be stimulated by compounds administered orally and also this has been shown that Carbonic anhydrase isozymes can be administered as growth factors of human stem cells, and hence an alternative to stem cell therapy in humans.

Carbonic anhydrase III has been used as an anti-oxidant in mice deficient in CA III gene. In IUBMB Life. 2004 June; 56(6): 343-7, Anti-oxidative response of Carbonic anhydrase III in skeletal muscle by Zimmerman U J, Wang P, Zhang X, Bognanovich S, Foster R

Description of Best Mode

REFERRING to FIG. 2, we observed two parallel paths of cell destruction that can be directly linked to deficiencies of cell-specific carbonic anhydrase enzymes, whether the decreased level of CA is a primary deficiency or secondary deficiency, as described therein. One path relates to the breakdown of the chemical reaction shown in Eq. 1 and the other relates to the release of caspase, leading to apoptosis. The result of both paths is dead and dying cells, which include brain cells and other neural cells. Here we show that at least one cause of the destruction of brain cells and other neurons is traceable to the decreased levels of cell specific carbonic anhydrase enzymes. Heretofore, researchers had identified only one of these parallel paths, the one involving caspase, Specifically, it has been reported in the Journal of Infectious Disease Diseases, 2000 September, 182 Suppl. 1:S85-92, by F. Chai, et al that the mechanism by which Zinc deficiency (equivalent to deficiency in Zinc carrying carbonic anhydrase enzyme) induces epithelial cell death involves the activation of caspase 3 as indicated in the right half of FIG. 2. The suggestion is made from this research that Zinc (i.e., CA) may suppress a step just before the activation of the caspase and a Zinc (i.e., CA) deficiency results in a failure to suppress that step.

The path illustrated on the left half of FIG. 2 shows decreased levels of CA (i.e., Zinc-carrying enzyme) upset the rate of reversible portion of the reaction indicated in Eq. 1, above, decreasing the formation of hydrogen ion that is the fuel for the ion pump that maintains the cell wall membrane, leading to depolarization and allowing neurotoxic substances to enter the cell, causing edema and cell death.

The path illustrated in FIG. 1C is newly presented in the instant invention. The decreased levels of Carbonic anhydrase isozymes leads to the decreased levels of hydrogen ions needed to neutralize the reactive oxygen species (ROS) produced as a result of aerobic respiration in the mitochondria of all living things and to neutralize all other reactive substances.

The path illustrated in FIG. 1B is newly presented in the instant invention, hydrogen ions produced by cell specific carbonic Anhydrase enzymes combines with adenosine diphosphate (ADP) to produce adenosine triphosphate (ATP) as fuel for all other cellular functions (H++ADP—ATP).

Whereas in aging, there has been observed a progressive decrease in levels of enzymes of which carbonic anhydrase is one, I believed that replenishing the carbonic anhydrase enzymes that catalyze the reversible reaction of Equation 1 will at least slow the progressive and gradual death of cells, including cells in the brain, which brain cell reduction is a major contributor to various age-related brain disorders in humans involving dementia such alzheimer's disease and other neurodegenerative diseases.

The progressive decrease of cell specific carbonic anhydrase enzymes also results in the progressive decrease of hydrogen ions which is acted upon by the cytochrome system which is needed to neutralize reactive substances including but not limited to reactive oxygen species (ROS) produced during cell respiration resulting in oxidative damage to all cellular and non-cellular structures, as illustrated in FIG. 1, hence the need to replenish the carbonic anhydrase isozymes in a subject.

Cell Specific Carbonic Anhydrase Enzymes I, II, III, IV, V, VI, VII have never used to restore to a higher level the Carbonic anhydrase enzymes that are lacking due to decreased levels due to normal aging, diseases associated with aging which includes oxidative stress or whether the replenishing enzymes are naturally produced and harvested or synthetically produced, nor has anyone used for this purpose any carbonic anhydrase stimulators to stimulate a patient's production of carbonic anhydrase enzymes.

As far as can be determined from the literature, one or more Cell Specific Carbonic Anhydrase enzymes have never been used as a treatment or prophylaxis for the treatment of immune diseases, whether administering one or more compounds that increases the level of one or more Cell Specific Carbonic Anhydrase enzymes that are present in decreased levels due to immune disorders of Humans.

Likewise No one has ever used one or more cell specific carbonic anhydrase enzymes as growth factors for human stem cells in treating human diseases, replacing the diseased or damaged human tissues or cells. Nobody has ever used one or more compounds which naturally generates the production of one or more cell specific carbonic anhydrase enzymes I, II, III, IV, V, VI and VII as growth factors for replacing damaged or diseased human cells or tissues and as growth factors of human stem cells whether they are adult or embryonic human stem cells, nor has anyone use this Carbonic anhydrase enzymes I, II, III, IV, V, VI and VII as an alternative for stem cell therapy.

Likewise no one has ever used one or more compounds that increases the level of one or more Cell specific Carbonic anhydrase I, II, III, IV, V, VI, VII as an anti-oxidant in treating diseases or conditions associated with oxidative stress in humans.

I have come to realization that administering supplemental cell specific carbonic anhydrase enzymes or administering cell specific carbonic anhydrase stimulators, diseases associated with oxidative stress can be prevented or treated. This can be achieved by maintaining the near normal levels of cell specific carbonic anhydrase enzymes of a patient by increasing the levels of one or more cell specific carbonic anhydrase enzymes that are present at reduced level in the tissue of the patient. This method can be done by directly administering the cell specific carbonic anhydrase enzymes themselves, administering one or more compounds that stimulates the natural production of one or more cell specific carbonic anhydrase I, II, III, IV, V, VI and VII enzymes that are present at reduced level in the tissue of a subject back to normal levels. Administering to the subject, additional doses of one or more Cell specific carbonic anhydrase isozymes I, II, III, IV, V, VI and VII to maintain them at normal levels.

Cell specific carbonic anhydrase isozymes can also be used as growth factors in treating diseases. This can be achieved by assaying which one or more cell specific carbonic anhydrase enzyme is or are present in the diseased or damaged subject's cell or organ to be treated and then, Administering one or more compounds that increases the level of one or more cell specific carbonic anhydrase I, II, III, IV, V, VI and VII that are present in a specific subject's cell or tissue to be replaced, either because of disease or from injury, then maintaining them at normal levels of the same Cell Specific Carbonic anhydrase enzymes from I, II, III, IV, V, VI, and VII that is present in the subject's cell or tissue to be replaced, diseased, or damaged.

This invention can be administered to patients exhibiting diseases associated with oxidative stress (oxidative damages on all cellular and non-cellular structures) as a therapeutic and prophylactic treatment. These diseases or conditions include but not are limited to to diabetes, arthritis, osteoporosis, hypertension, abnormal lipids, systemic lupus erythematosus, atherosclerosis, amyloid disease, cystic fibrosis, arteriosclerosis, wrinkling of the skin, myopathies including cardiomyopathies, endothelial dysfunctions, cancer, chronic neurodegenerative diseases which includes but not limited to autism, huntington's disease, alzheimer's disease, multiple Sclerosis, parkinson's disease, Lou Gehrig disease. This invention includes cancer of the breast, colon, prostate, ovary and other diseases associated with oxidative stress.

Oxidative stress is characterized by decreased level of hydrogen ions produced as a result of decreased levels of carbonic anhydrase isozymes, which maybe due to normal aging or accelerated aging. Treating this condition can be achieved by measuring first the levels of Malondialdehyde (MDA), use of monoclonal antibodies, liquid chromography, creatine kinase before and after administering a compound that increases the level of Cell Specific Carbonic Anhydrase I, II, III, IV, V, VI, VII, other methods are available.

Thus, I disclose here a method for the treatment and prophylaxis of diseases associated with oxidative stress associated with a decrease presence of one or more cell specific carbonic anhydrase I, II, III, IV, V, VI and VII in the tissue of a patient, which method comprises administering over an extended of time in the range of six months until the patient dies, a pharmaceutically effective, non toxic amount of one or more compounds that increases the level of one or more cell specific carbonic anhydrase enzymes in the tissue of a patient back to normal levels.

The compound used could be the cell specific carbonic anhydrase that is believed to be evidencing decreased presence as measured in the blood tests or in cell cultures from biopsied tissues or from the cerebro-spinal fluid. Alternatively, the compound used could be synthetically produced cell specific carbonic anhydrase enzymes. As, alternative the compound used could be naturally produced cell specific carbonic anhydrase enzymes. Yet another alternative allows that the compound used is a compound that, when administered to a subject, promotes the natural production of the cell specific carbonic anhydrase enzyme that is evidencing decreased presence as measured in blood test or in cell cultures in biopsied tissues or from the cerebro-spinal fluid. The compound itself need not be the one that passes the blood brain barrier; the cell specific carbonic anhydrase enzyme need not be produced in the brain for it is known to pass the blood brain barrier so the promoting of natural production of cell specific carbonic anhydrase enzyme can take place elsewhere in the body.

Examples of compounds that are known to increase the production of the required cell specific carbonic anhydrase enzymes include but are not limited to Zinc, growth hormones, androgens including DHEA (dehydroepiandrosterone); sex hormones which includes but not limited to estrogen, testosterone, acetylcholine, melatonin, Vitamin D3, NSAID, cysteamine, phorbol myristate acetate, histamine; L and D phenylalanine serotonin and serotonin re-uptake inhibitors. Zinc increases the production of Carbonic anhydrase VI, growth hormones increases the production of Carbonic anhydrase II and III, NSAID increases the production of Carbonic anhydrase I, and II, sex hormones estrogen, testosterone increases the production of carbonic anhydrase III, Vitamin D3 increases the production of Carbonic anhydrase II, Histamine and cysteamine increases the production of carbonic anhydrase I, II, IV, the selective serotonin reuptake inhibitors which includes sertraline, fluoxetine, citalopram increases the production of carbonic anhydrase I, II; acetylcholine increases the production of carbonic anhydrase II, IV; serotonin and melatonin increases the production of CA I, II, L and D phenylalanine increases the production of carbonic anhydrase I, II, V (A) and VII Administering the compound maybe done but not limited to injection or ingestion. The injection method used maybe intramuscular or intravenous, dissolved in a sterile saline solution, glucose solution, or other commonly administered parenteral solution. The best method of administering the compound will be learned with modest experimentation. The individual patient's response to the compound will be learned through testing for the cell specific enzyme in blood samples taken before and after administering the medication and by enzyme levels measured from cell cultures of biopsied tissues from the patient or found in the cerebro-spinal fluid. The goal is to increase the tissue level of cell specific carbonic anhydrase enzymes from a decreased level in the tissue of a patient to a more normal level. Insofar as the enzyme in the blood is a reflection of the enzyme level in the tissue of a patient, the blood test may be a sufficient indicator. In addition, other means of measuring enzyme levels that are known to the practitioner maybe employed.

For the use of cell specific carbonic anhydrase enzymes as growth factors, the main objective is to keep the cell specific carbonic at normal levels in the damaged or diseased tissue as an environment for them to differentiate and grow. This can be done by determining first, which one or more cell specific carbonic anhydrase enzymes are present in the diseased or damaged human tissue then administering a non toxic amount of one or more compounds that increases the level of one or more cell specific carbonic anhydrase enzymes that is present in the damaged or diseased human tissue. Then maintaining the cell specific carbonic anhydrase enzymes at normal levels. Measuring the level of one or more cell specific carbonic anhydrase enzymes can be done directly from the damaged or diseased tissue. Other methods known can be used by the practitioner.

Response to the treatment can be assessed by doing biopsy of the tissues, imaging of the tissues which includes magnetic resonance imaging (MRI), amelioration of the signs and symptoms, these procedures are done before and after treatment. Other methods are available to the one who are skilled in the art.

Pharmaceutical composition suitable for use in the invention include compositions suitable wherein the active ingredient are contained in an effective amount to achieved the intended purpose. The determination of an effective dose is well within the capability of those skilled in the art.

A therapeutically effective dose refers to that amount of active ingredient that ameliorates the symptoms or condition, the condition being caused by or reflected in the reduced concentration of carbonic anhydrase. Therapeutic efficacy and toxicity maybe determined by standard procedures from blood testing, from biopsied tissues, and by other means known to the practitioner, for comparison with the normal values. The dosage is preferably within the range of circulating concentrations that are efficacious with little or no toxicity. The dosage varies within this range depending upon the dosage form employed, sensitivity of the patient and the route of administration.

The exact dosage will be determined by the practitioner, in light Of factors related to the subject that requires treatment. Dosage and administration are adjusted to provide sufficient levels of the active moiety or to maintain the desired effect, which is a near-normal level of the cell specific carbonic anhydrase enzyme. Factors which maybe taken into account include the severity of the increased or reduction extant in the subject, general health of the subject, age, weight and gender of the subject, diet, time and frequency of administration, drug combination(s), reaction, sensitivities, and tolerance/response to therapy. Long acting pharmaceutical compositions may be administered every 3 to 4 days, every week, or once every two weeks depending on the half-life and clearance rate of the particular formulation.

Normal dosage amounts may vary from 0.1 to 100,000 micrograms, up to a total dose of about one gram, depending upon the route of administration. Guidance as to particular dosages and methods of delivery is provided in the literature and generally available to practitioners in the art. Those skilled will employ different formulations to achieve the desired results.

I claim:

1. A method for the treatment of condition of aging associated with a decreased presence of one or more carbonic anhydrase enzymes, which method comprises the following steps:
   (a) identifying a subject who is exhibiting signs of Alzheimer's disease;
   (b) measuring and identifying which one or more of carbonic anhydrase enzymes I (CA-I), II (CA-II), III (CA-III), IV (CA-IV), V (CA-V), VI (CA-VI) and VII (CA-VII) are present at decreased levels in the blood, brain cells, or cerebrospinal fluid of said subject;
   (c) administering to a subject who has been identified with decreased levels of CA-II in step (b) an effective, non-toxic amount of vitamin $D_3$ to increase the levels of CA-II; and
   (d) further administering to the subject an effective, non-toxic amount of an active ingredient selected from the group consisting of zinc, indomethacin, phorbol myristate acetate and cysteamine to increase the levels of other carbonic anhydrase enzymes; wherein steps (c) and (d) are carried out for an extended period of time in the range of six months to five years.

2. The method of claim 1, wherein vitamin $D_3$ promotes the natural production of CA-II.

3. The method of claim 1, wherein the administering and further administering steps are by injection, intramuscular, intravenous and/or ingestion.

4. The method of claim 1, wherein step (b) is carried out with the blood of the subject.

5. The method of claim 1, wherein step (b) is carried out with the brain cells of the subject.

6. The method of claim 1, wherein step (b) is carried out with biopsied brain tissues of the subject.

7. The method of claim 1, wherein step (b) is carried out with the cerebrospinal fluid of the subject.

8. The method of claim 1, wherein the subject is human.

* * * * *